United States Patent [19]
Chien

[11] Patent Number: 6,113,530
[45] Date of Patent: Sep. 5, 2000

[54] MAGNETIC ACUPUNCTURE EQUIPMENT

[76] Inventor: Nai-Hsin Chien, 340 Azusa St., #B, Los Angeles, Calif. 90012

[21] Appl. No.: 09/184,681

[22] Filed: Nov. 2, 1998

[51] Int. Cl.[7] .............................. A61N 2/00; A61H 7/00
[52] U.S. Cl. ............................. 600/9; 606/189; 606/204
[58] Field of Search ........................... 600/975; 128/907; 606/189, 204

[56]                  References Cited
              U.S. PATENT DOCUMENTS
    5,782,858   7/1998   Cheng ..................................... 606/204

*Primary Examiner*—John P. Lacyk
*Attorney, Agent, or Firm*—Raymond Y. Chan; David and Raymond

[57] ABSTRACT

A magnetic acupuncture equipment which is adapted for substitute the conventional acupuncture needles comprises a magnetic acupuncture pen. The magnetic acupuncture pen includes a tubular housing made of magnetic conducting material, an insulation member disposed inside the housing, a first and a second permanent magnet respectively disposed at two ends of the insulation member inside the housing, a first acupuncture member secured to a first end of the housing, and a second acupuncture member secured to a second end of the housing. The inner ends of the first and second permanent magnets, which are adjacent to the two ends of the insulation member respectively, have the same magnetic pole. In other words, the outer ends of the first and second permanent magnets, which are respectively located near the first and second acupuncture members, also have the same magnetic pole. The first acupuncture member has an acute head providing an acupuncture point adapted to massage and press on a specific acupoint on a human body to provide stimulation.

10 Claims, 4 Drawing Sheets

MAGNETIC ACUPUNCTURE EQUIPMENT

FIELD OF THE PRESENT INVENTION

The present invention relates to a kind of acupuncture equipment, and more particularly to a magnetic acupuncture equipment which can provide stimulation to a particular human acupoint instead of piercing the human body by acupuncture needles or passing electric pulses to the human body by the electrical acupuncture equipment.

BACKGROUND OF THE PRESENT INVENTION

It is well known that there are acupoints located at specific positions of a human body based on the oriental medical science. Adequate simulation to a specific acupoint may result in particular health or medical effects, such as relieving pain and enhancing metabolism, to improve human health.

Acupuncture needle is the traditional tool for acupoint stimulation. In order to stimulate the specific acupoint on a human body, an acupuncture needle is required to pierce into the human body. However, since AIDS may infect through used or polluted needle, people nowadays are basically unwilling to pierce anything into their body. Even for medicine injection, most people would try their best to minimize the chance. Moreover, unlike the medicine injection that one can inject the medicine into any portion of the muscle or blood vessels, only experienced oriental doctor can exactly know where is the specific acupoint. Since some portions of the human body are crowd with acupoints and a needle is actually pierced into the human body, unexpected injury or adverse effect may occur if the acupuncture needle is pierced into a wrong position of a human body.

Another conventional tool used for stimulating acupoint is a kind of electrical acupuncture equipment adapted for applying intermittent electric pulses at the specific acupoint on human body for simulation. Electrical acupuncture equipment avoids foreign object such as acupuncture needle piercing into the human body. Similarly, the electrical acupuncture equipment still has a risk of wrongfully applying the electric pulse at a wrong position on body or wrongfully applying an electric current that is too strong for the patient and causes unexpected injury.

SUMMARY OF THE PRESENT INVENTION

In fact, nobody will explode himself or herself in an electrical field but everybody is unavoidably exploded within all kinds of magnetic field. It would be an excellent concept to use magnetic power to substitute the electric power for stimulation purpose in acupuncture science. However, how to concentrate and focus the magnetic energy to a specific acupoint on human body becomes the biggest unsolved problem in the acupuncture science.

Accordingly, it is a main object of the present invention to provide a magnetic acupuncture equipment capable of focusing and concentrating the magnetic power to a particular point adapted for stimulating a specific acupoint on human body.

A further object of the present invention is to provide a magnetic acupuncture equipment which further comprises a magnetic enhancing device for enhancing the magnetic strength and piercing ability of the magnetic acupuncture equipment.

Yet another object of the present invention is to provide a magnetic acupuncture equipment which use magnetic power instead of electrical power or needle piercing to simulate the acupoint of human body, so that it is free of risk of doing any injury to human body even it is operated by a non-experienced person. Therefore, the magnetic acupuncture equipment of the present invention is especially suitable to be designed in family kit for family members to use for general purposes such as pain relief and muscle massage.

Still another object of the present invention is to provide a magnetic acupuncture equipment which is easy to operate and maintain.

In order to accomplish the above objects, the present invention provides a magnetic acupuncture equipment which comprises a magnetic acupuncture pen and a magnetic enhancing device.

The magnetic acupuncture pen comprises a tubular housing made of magnetic conducting material, an insulation member disposed inside the housing, a first and a second permanent magnet respectively disposed at two ends of the insulation member inside the housing, a first acupuncture member secured to a first end of the housing, and a second acupuncture member secured to a second end of the housing. The inner ends of the first and second permanent magnets, which are adjacent to the two ends of the insulation member respectively, have the same magnetic pole. In other words, the outer ends of the first and second permanent magnets, which are respectively located near the first and second acupuncture members, also have the same magnetic pole. The first acupuncture member has an acute head providing an acupuncture point adapted to massage and press on a specific acupoint on a human body to provide stimulation.

The magnetic enhancing device comprises a case made of magnetic conducting material, a magnetic field generator which is installed inside the case for generating magnetic waves transmitting between two poles of the magnetic field generator. Therefore, when the magnetic enhancing device is positioned near to the magnetic acupuncture pen, especially to the first and the second acupuncture member at two ends thereof, the magnetic waves generated by the magnetic enhancing device will substantially induce the magnetic intensity and the magnetic piercing ability of the magnetic acupuncture pen so as to enhance the stimulation on the pressing acupoint.

DETAILED DESCRIPTION OF THE PREFERRED EMBODIMENT

Figure 1:
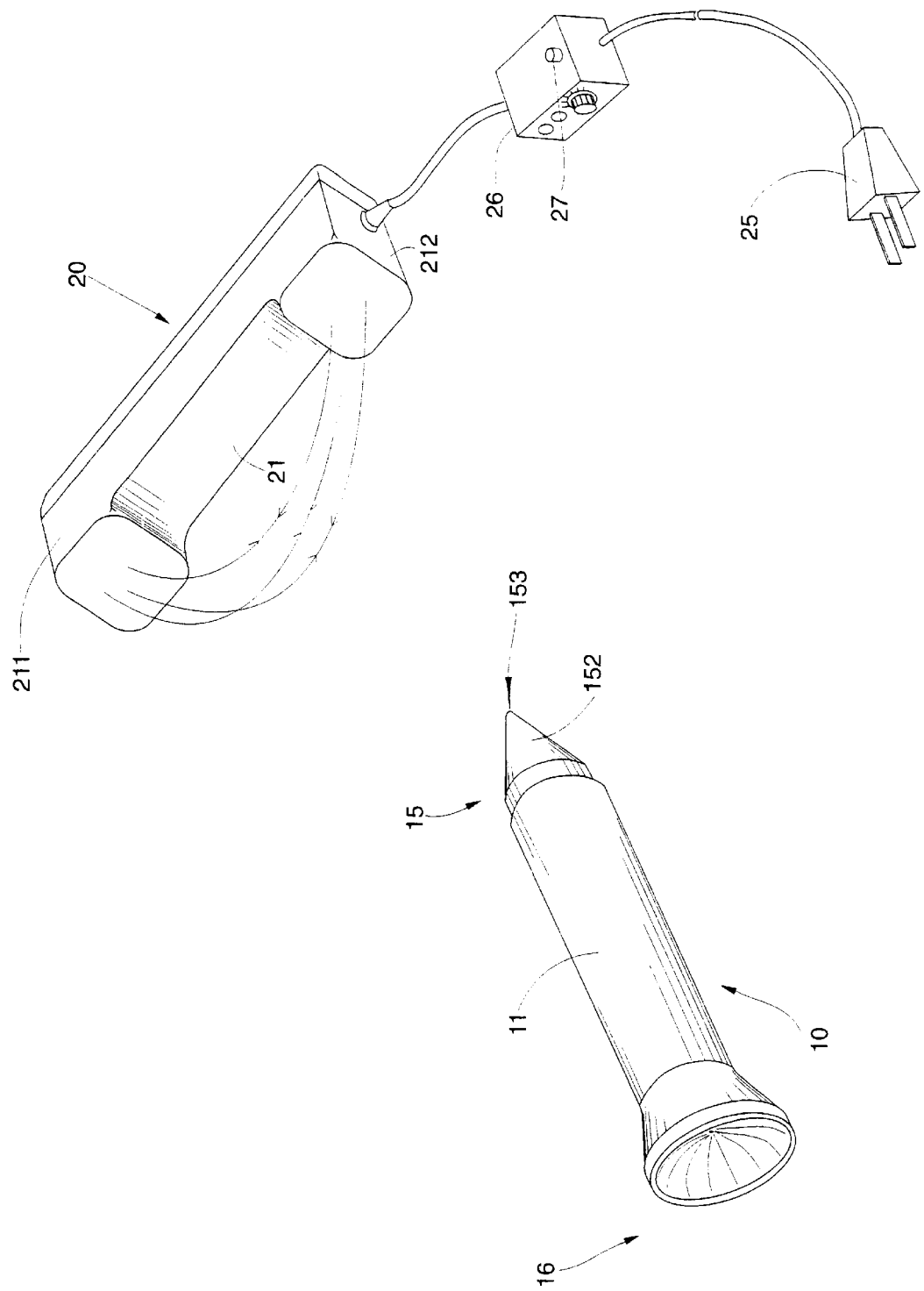
FIG. 1 is a perspective view of a magnetic acupuncture equipment in accordance with a preferred embodiment of the present invention.
Figure 2:
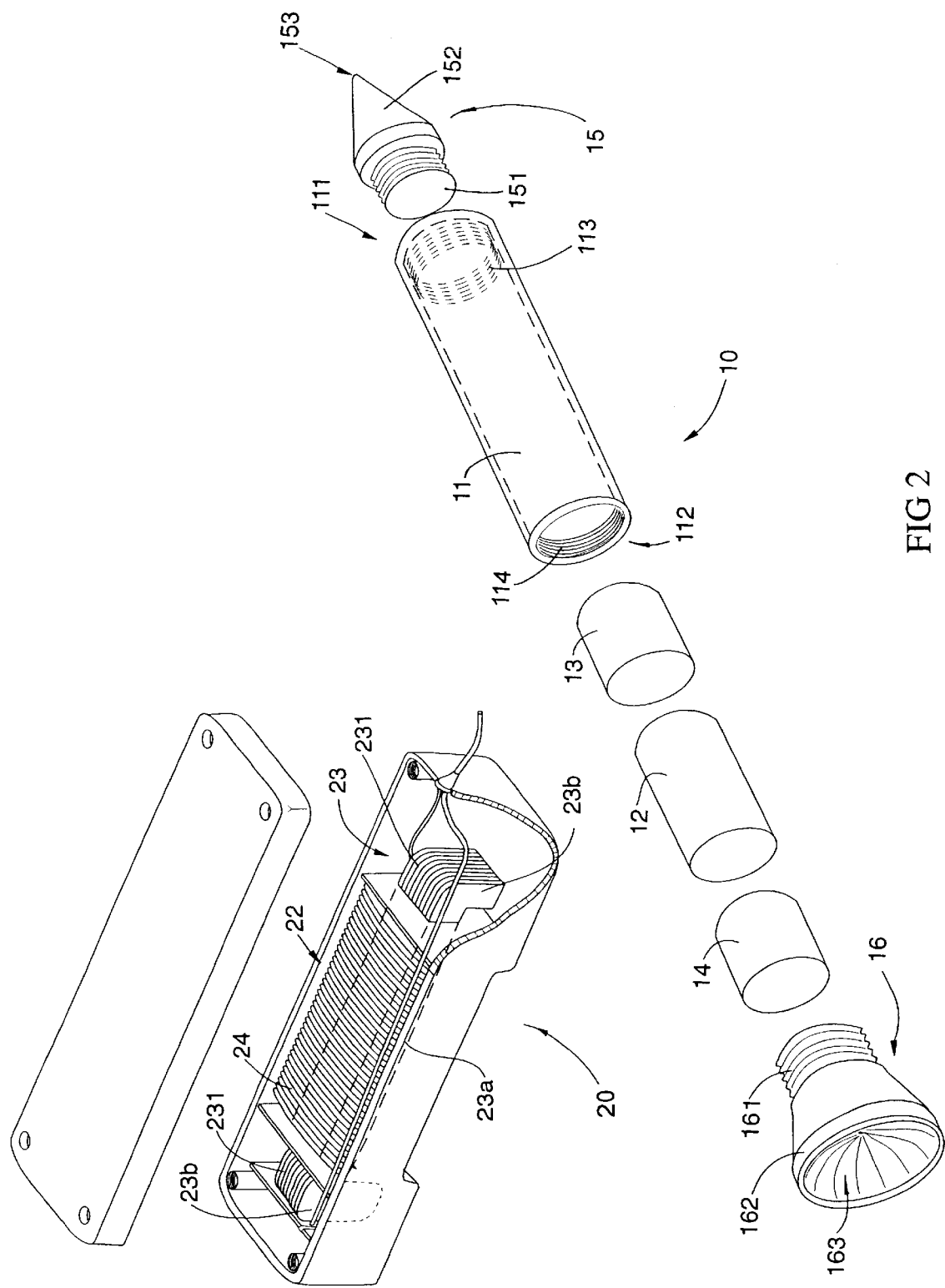
FIG. 2 is an exploded view of the magnetic acupuncture equipment according to the above preferred embodiment of the present invention.
Figure 3:
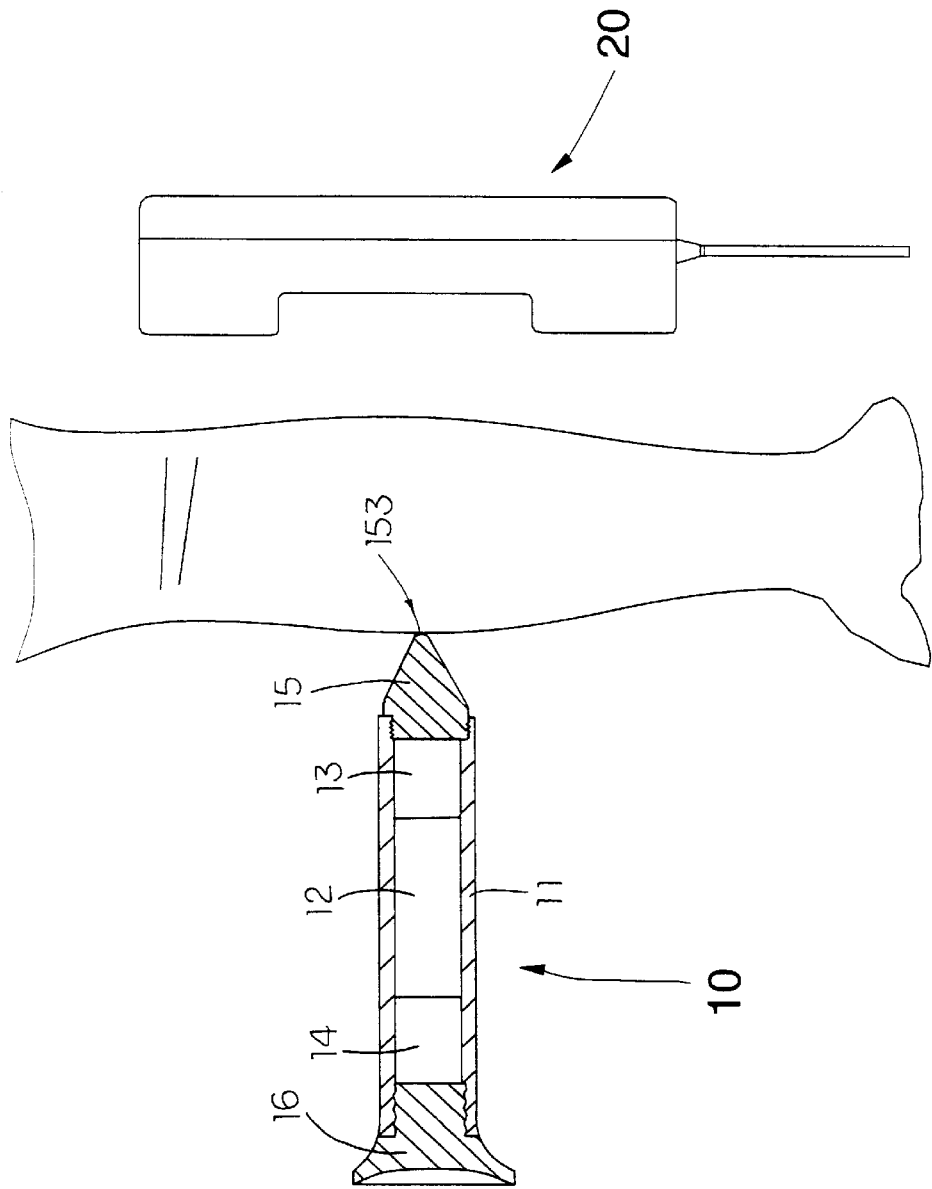
FIG. 3 is a sectional view of the magnetic acupuncture equipment while applying to a specific acupoint of a human body according to the above preferred embodiment of the present invention.

Referring to FIGS. 1 to 3, a magnetic acupuncture equipment according to a preferred embodiment of the present invention is illustrated, which comprises a magnetic acupuncture pen 10. The magnetic acupuncture pen 10 comprises a tubular housing 11 made of magnetic conducting material, an insulation member 12 which is made of magnetic insulating material and disposed inside the housing 11, a first permanent magnet 13 disposed at one end of the insulation member 12 inside the housing 11, a second permanent magnet 14 disposed at another end of the insulation member 12 inside the housing 11, a first acupuncture member 15 secured to a first end 111 of the housing 11, and a second acupuncture member 16 secured to a second end 112 of the housing 11.

According to the present embodiment, the housing is a cylindrical tube having a predetermined diameter and length. The insulation member 12, the first permanent magnet 13 and the second permanent magnet 14 are all in cylindrical shape, each of them has a diameter equal to or slightly smaller than the inner diameter of the housing 11 adapted to fittedly received inside the housing 11. The first and second ends 111, 112 of the housing 11 respectively provide a first and a second threaded portion 113, 114. The first permanent magnet 13 is positioned near the first end 111 of the housing 11. The second permanent magnet 14 is positioned near the second end 112 of the housing 11. The insulation member 12 is positioned between the first permanent magnet 13 and the second permanent magnet 14. The total length of the insulation member 12 and the first and second permanent magnets 13, 14 is preferred equal to the length between the first end 111 and the second end 112 of the housing 11.

The inner ends of the first and second permanent magnets 13, 14, which are adjacent to the two ends of the insulation member 12 respectively, are arranged to have the same magnetic pole. In other words, the outer ends of the first and second permanent magnets 13, 14, which are respectively located near the first and second acupuncture members 15, 16, are also arranged to have the same opposite magnetic pole.

According to the preferred embodiment of the present invention, both the two outer ends of the first and second permanent magnets 13, 14 are north pole having a magnetic intensity of 400 guass while the two inner ends of the first and second permanent magnets 13, 14 are south pole having a magnetic intensity of 380 guass. The magnetic intensity between the north pole and the south pole of each of the first and second permanent magnets 13, 14 is 250 guass.

The first acupuncture member 15 has a connecting end 151 and an acute head 152 providing an acupuncture point 153 adapted to massage and press on a specific acupoint on a human body to provide stimulation. The connecting end 151 has connecting threads provided thereon for screwing to the first threaded portion 113 of the first end 111 of the housing 11. The acute head 152 reduces its diameter while extending coaxially from the connecting end 151 so as to form the acupuncture point 153 at its tip end. Different degrees of sharpness of the acupuncture point 153 can provide different acupuntural effects. The user may prepare several first acupuncture members 15 each having an acupuncture point 153 with different sharpness. Therefore, the user may selectively replace the desired first acupuncture member 15 according to different patients and situations.

As, shown in FIG. 3, the design of the acute head 152 and the acupuncture point 153 is to facilitate the user to precisely press against the specific acupoint on human body, such as "HEGU", "QUCHI", "XIGUAN", "SANYINJIAO", "LONGU", "CHENGQI", "SIBAI", "TINGHU", "FUBM", "YANGBAM", "YANGJIAO", "WAIQIU", "YIFENG", "QIMAI", "JIAOSUN", "ERMEN", "ERHELIAO", "SIZHUKONG", or "TINGGONG".

Moreover, the strong magnetic field around the first permanent magnet 13 provides magnetic waves with high magnetic intensity, which will be concentrated and focused at the contact point between the human body and the acupuncture point 153, so that strong magnetic energy will penetrate the human body through the specific acupoint to provide adequate stimulation to that acupoint of the human body. Another function of the acute head 152 and the acupuncture point 153 is to enable the user pressing against the muscle and massaging the muscle with that acupuncture point 153 so as to stimulate the acupoint and the muscle around. The stimulated muscle nerves will transmit messages to the brain. The brain stem's nerves will send out messages back to temporarily relax the stimulated muscle and/or other reflecting organs or portions of the human body. Therefore, similar to the effect of message, the repeated stimulation and relaxation of the respective muscle, in fact, can exercise the respective muscle.

Figure 4:
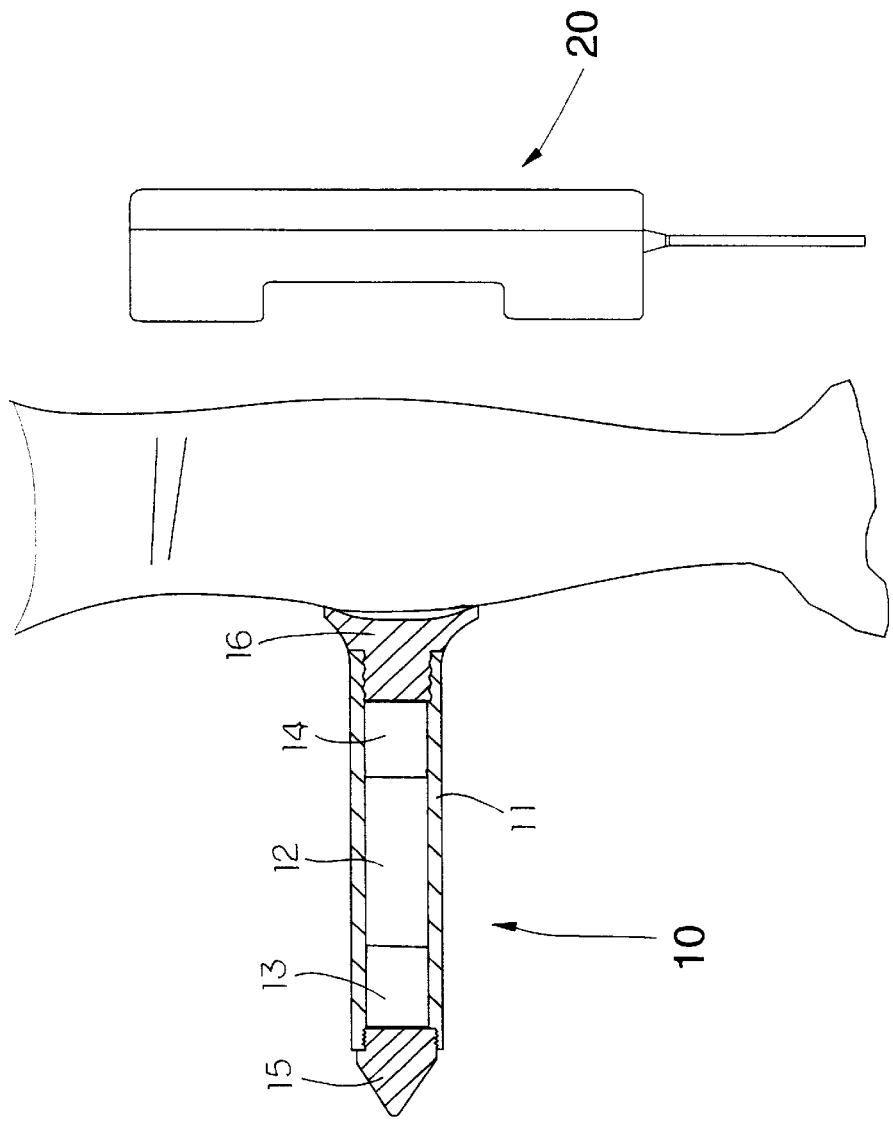
FIG. 4 is a sectional view of the magnetic acupuncture equipment while applying to a larger portion of a human body according to the above preferred embodiment of the present invention.

The second acupuncture member 16 has a connection end 161 having connection threads thereon for screwing to the second threaded portion 114 of the of the second end 112 of the housing 11. The second acupuncture member 16 further has an acupuncture head 162 integrally extended from the connection end 161. The acupuncture head 162 is in bowl shape that gradually increases its diameter and forms a circular concave groove 163 at a free end thereof As shown in FIG. 4, the acupuncture head 162 is served for pressing against a specific larger body portion of the human body with the concave groove 163 facing the human body. The magnetic waves around the second permanent magnet 14 will be concentrated inside the concave groove 163 to stimulate the body portion covered by the acupuncture head 162. For example, the user may use the acupuncture head 162 to cover an eye, so that the magnetic energy will stimulate the muscles around the eye ball. As mentioned in the above paragraph, the repeated stimulation and relaxation of the muscles around the eye ball will relax and exercise such muscles. Moreover, to those non-experienced user who may find difficult to precisely locate the specific acupoint. Then the user may simply use the acupuncture head 162 to cover the approximate portion of the human body.

To some patients, stronger magnetic energy may need to use for stronger stimulation. The magnetic acupuncture equipment of the present invention further comprises a magnetic enhancing device 20 adapted for enhancing the magnetic intensity of the magnetic acupuncture pen 10. The magnetic enhancing device 20 comprises a case 21, a magnetic field generator 22 which is installed inside the case 21 for generating magnetic waves transmitting between two poles 221, 222 of the magnetic field generator 22.

The case 21 has two pole chambers 211, 212 at two ends thereof, wherein the two pole chambers 211, 212 are facing towards the same direction and are made of magnetic conducting material. The magnetic field generator 22 comprises a U-shaped core 23 which comprises a plurality of U-shaped silicon steel plates 231 overlapping layer by layer. The core 23 has a central core shank 23a and two pole wings 23b perpendicularly extending from two ends of the core shank 23a in the same direction. The magnetic field generator 22 further comprises a conduction wire 24 which is made of brass being wrapped around the core shank 23a and an AC power source 25 is connected to two ends of the brass wire 24. According to the preferred embodiment, the AC power source 25 is an electric plug for connecting to an AC power socket (not shown). The two pole wings 23b are respectively received in the two pole chambers 211, 212 of the case 21 when the magnetic field generator 22 is installed inside the case 21.

When AC electric current is conducted through the conduction wire 24, the core 23 will be induced to generate an open type magnetic field, wherein the magnetic waves of the magnetic field would flow between the two pole wings 23b. According to the preferred embodiment, the internal resistance of the conduction wire 24 is 169Ω/120Hz measured along the length and 5.6Ω/120Hz measured radially, and that the magnetic intensity measured at the two pole wings 23b is preferred to be set at 450 to 500 guass respectively.

If adjustable magnetic intensity is preferred for the magnetic field generator 22, the magnetic field generator 22 may further comprises an adjustable transformer 26 connected to the AC power source 25. A fuse 27 may further connected to the conduction wire 24 to prevent unwanted damage to the equipment during power shock.

Base on the reversal of magnetism between magnetic fields, when the magnetic enhancing device is positioned near to the magnetic acupuncture pen, especially to the first and the second acupuncture member at two ends thereof (preferable 2 to 10 cm), reverse magnetic resonance occurred, so that the magnetic waves generated by the magnetic enhancing device 20 will substantially induce the magnetic intensity and the magnetic piercing ability of the magnetic acupuncture pen 10 so as to enhance the stimulation on the acupoint to be pressed.

In view of above, the magnetic acupuncture equipment of the present invention can be used to substitute the conventional acupuncture needles and the electrical acupuncture equipment in acupuncture science. The following features can be achieved:

1. The magnetic acupuncture equipment is capable of focusing and concentrating the magnetic power to a particular point adapted for stimulating a specific acupoint on human body.
2. The magnetic enhancing device can further enhance the magnetic strength and piercing ability of the magnetic acupuncture equipment.
3. The present invention utilizes magnetic power instead of electrical power or needle piercing to simulate the acupoint of human body, so that it is free of risk of doing any injury to human body even it is operated by a non-experienced person. Therefore, the magnetic acupuncture equipment of the present invention is especially suitable to be designed in family kit for family members to use for general purposes such as pain relief and muscle massage.
4. It is easy to operate and maintain.

What is claimed is:

1. A magnetic acupuncture equipment, comprising:
   a magnetic acupuncture pen which comprises a tubular housing made of magnetic conducting material, an insulation member which is made of magnetic insulating material and disposed inside said housing, a first permanent magnet disposed at one end of said insulation member inside said housing, a second permanent magnet disposed at another end of said insulation member inside said housing, a first acupuncture member secured to a first end of said housing, and a second acupuncture member secured to a second end of said housing, wherein two inner ends of said first and second permanent magnets which are adjacent to said two ends of said insulation member respectively, are arranged to have the same magnetic pole, and two outer ends of said first and second permanent magnets, which are respectively positioned near said first and second acupuncture members, are also arranged to have the same opposite magnetic pole, wherein said first acupuncture member has an acute head providing an acupuncture point for massaging and pressing on a specific acupoint on a human body, and
   a magnetic enhancing device adapted for enhancing the magnetic intensity of said magnetic acupuncture pen, wherein said magnetic enhancing device comprises a case and a magnetic field generator which is installed inside said case for generating magnetic waves transmitting between two poles of said magnetic field generator.

2. A magnetic acupuncture equipment, as defined in claim 1, wherein said magnetic field generator comprises a U-shaped core which has a central core shank and two pole wings perpendicularly extending from two ends of said core shank in same direction, a conduction wire wrapped around said core shank, and an AC power source which is connected to two ends of said brass wire.

3. A magnetic acupuncture equipment, as defined in claim 2, wherein said U-shaped core comprises a plurality of U-shaped silicon steel plates overlapping layer by layer.

4. A magnetic acupuncture equipment, as defined in claim 3, wherein said AC power source is an electric plug for connecting to an AC power socket, and said case has two pole chambers at two ends thereof, which are facing towards the same direction and are made of magnetic conducting material, wherein said two pole wings are respectively received in said two pole chambers of said case when said magnetic field generator is installed inside said case.

5. A magnetic acupuncture equipment, as defined in claim 4, wherein said magnetic field generator further comprises an adjustable transformer connected to said AC power source.

6. A magnetic acupuncture equipment, as defined in claim 5, wherein a fuse is connected to said conduction wire.

7. A magnetic acupuncture equipment, comprising:
   a magnetic acupuncture pen which comprises a tubular housing made of magnetic conducting material, an insulation member which is made of magnetic insulating material and disposed inside said housing, a first permanent magnet disposed at one end of said insulation member inside said housing, a second permanent magnet disposed at another end of said insulation member inside said housing, a first acupuncture member secured to a first end of said housing, and a second acupuncture member secured to a second end of said housing, wherein two inner ends of said first and second permanent magnets which are adjacent to said two ends of said insulation member respectively, are arranged to have the same magnetic pole, and two outer ends of said first and second permanent magnets, which are respectively positioned near said first and second acupuncture members, are also arranged to have the same opposite magnetic pole, wherein said first acupuncture member has an acute head providing an acupuncture point for massaging and pressing on a specific acupoint on a human body, wherein said second acupuncture member has a bowl shaped acupuncture head that gradually increases a diameter thereof and forms a circular concave groove at a free end thereof, and
   a magnetic enhancing device adapted for enhancing the magnetic intensity of said magnetic acupuncture pen, wherein said magnetic enhancing device comprises a case and a magnetic field generator which is installed inside said case for generating magnetic waves transmitting between two poles of said magnetic field generator.

8. A magnetic acupuncture equipment, as defined in claim 7, wherein said magnetic field generator comprises a U-shaped core which has a central core shank and two pole wings perpendicularly extending from two ends of said core shank in same direction, a conduction wire wrapped around said core shank, and an AC power source which is connected to two ends of said brass wire.

9. A magnetic acupuncture equipment, as defined in claim 8, wherein said U-shaped core comprises a plurality of U-shaped silicon steel plates overlapping layer by layer, and said AC power source is an electric plug for connecting to an AC power socket, and said case has two pole chambers at two ends thereof, which are facing towards the same direction and are made of magnetic conducting material, wherein said two pole wings are respectively received in said two pole chambers of said case when said magnetic field generator is installed inside said case.

10. A magnetic acupuncture equipment, as defined in claim 9, wherein said magnetic field generator further comprises an adjustable transformer connected to said AC power source, and that a fuse is connected to said conduction wire.

* * * * *